United States Patent [19]

Kronenthal et al.

[11] Patent Number: 5,629,429

[45] Date of Patent: May 13, 1997

[54] PROCESS FOR PREPARING 4-ARYLAMINO-BENZOPYRAN AND RELATED COMPOUNDS

[75] Inventors: David R. Kronenthal, Yardley, Pa.; Richard H. Mueller, Ringoes; Jollie D. Godfrey, Jr., Trenton, both of N.J.

[73] Assignee: Bristol-Myers Squibb Company, Princeton, N.J.

[21] Appl. No.: 486,111

[22] Filed: Jun. 7, 1995

[51] Int. Cl.$^6$ .................. C07D 233/02; C07D 233/04; C07D 233/54

[52] U.S. Cl. .................. 548/311.4; 549/399; 549/404

[58] Field of Search .................. 548/311.4, 454, 548/305.1; 549/399, 404; 544/238, 58.7, 62, 151, 376; 546/196, 167

[56] References Cited

U.S. PATENT DOCUMENTS

| | | | |
|---|---|---|---|
| 3,330,838 | 7/1967 | Augstein et al. | 260/309.6 |
| 3,812,157 | 5/1974 | Lin et al. | 260/345.2 |

(List continued on next page.)

FOREIGN PATENT DOCUMENTS

| | | | |
|---|---|---|---|
| 0076075 | 4/1983 | European Pat. Off. | 514/456 |
| 0091748 | 10/1983 | European Pat. Off. | 514/456 |
| 0093535 | 11/1983 | European Pat. Off. | 514/456 |
| 0120427 | 10/1984 | European Pat. Off. | 514/456 |
| 0126311 | 11/1984 | European Pat. Off. | 514/456 |
| 0139992 | 5/1985 | European Pat. Off. | 514/456 |
| 0205292 | 12/1986 | European Pat. Off. | 514/456 |
| 0214818 | 3/1987 | European Pat. Off. | 514/456 |
| 0247266 | 12/1987 | European Pat. Off. | 514/456 |
| 0250077 | 12/1987 | European Pat. Off. | 514/456 |
| 0274821 | 7/1988 | European Pat. Off. | 514/456 |
| 0287196 | 10/1988 | European Pat. Off. | 514/456 |
| 0339562 | 11/1989 | European Pat. Off. | 514/456 |
| 0344747 | 12/1989 | European Pat. Off. | 514/456 |
| 0350805 | 1/1990 | European Pat. Off. | 514/456 |
| 0351767 | 1/1990 | European Pat. Off. | 514/456 |
| 0359537 | 3/1990 | European Pat. Off. | 524/456 |
| 0377966 | 7/1990 | European Pat. Off. | 514/456 |
| 0377967 | 7/1990 | European Pat. Off. | 514/456 |
| 0385584 | 8/1990 | European Pat. Off. | 514/456 |
| 0389861 | 10/1990 | European Pat. Off. | 5214 456 |
| 0401010 | 12/1990 | European Pat. Off. | 514/456 |
| 0402716 | 12/1990 | European Pat. Off. | 514/456 |
| 0407200 | 1/1991 | European Pat. Off. | 514/456 |
| 0412531 | 2/1991 | European Pat. Off. | 514/456 |
| 0431741 | 6/1991 | European Pat. Off. | 514/456 |
| 0462761 | 12/1991 | European Pat. Off. | 514/456 |
| 0488616 | 6/1992 | European Pat. Off. | 514/456 |
| 0501797 | 9/1992 | European Pat. Off. | 514/456 |
| 0525768 | 2/1993 | European Pat. Off. | 514/456 |
| 2801187 | 7/1978 | Germany | 514/456 |
| 2204868 | 11/1988 | United Kingdom | 514/456 |
| WO8707607 | 12/1987 | WIPO | 514/456 |
| WO89/09217 | 10/1989 | WIPO | 514/456 |
| WO91/09031 | 6/1991 | WIPO | 514/456 |
| WO92/05174 | 4/1992 | WIPO | 514/456 |
| WO92/14733 | 9/1992 | WIPO | 514/456 |
| WO92/22293 | 12/1992 | WIPO | 514/456 |

OTHER PUBLICATIONS

A. P. Terent'ev et al., "Optically Active Isocyanates, III. Synthesis and Spectropolarimetric Study of Optically Active N-derivative of Urea", *Chemical Abstracts*, vol. 71, Abstract No. 69992h, p. 250 (1969).

J. Bermudez et al., "5-Hydroxytryptamine (5-HT$_3$) Receptor Antagonists. 2. 1-Indolinecarboxamides", *J. Med. Chem.*, vol. 33, pp. 1929–1932 (1990).

P. D. Leeson et al., "4-Amido-2-carboxytetrahydroquinolines, Structure-activity Relationships for Antagonism at the Glycine Site of the NMDA Receptor", *J. Med. Chem.*, vol. 35, pp. 1954–1968 (1992).

J. L. Hughes et al., "Cardiovascular Activity of Aromatic Guanidine Compounds", *J. Med. Chem.*, vol. 18, No. 11, pp. 1077–1088 (1975).

M. Mazza et al., "N-Acilindoline Ad Attivita Fitotossica", *Farmaco. Ed. Sci.*, vol. 31, No. 10, pp. 746–754 (1976).

T. Sekiya et al., "Benzene-condensed Cyclic Amine β-amino Carboxamides as Antichycardiacs and Vasodilators", *Chemical Abstracts*, vol. 113, p. 694 (1990).

(List continued on next page.)

*Primary Examiner*—Floyd D. Higel
*Attorney, Agent, or Firm*—Ellen K. Park

[57] ABSTRACT

A method of preparing compounds of the formula

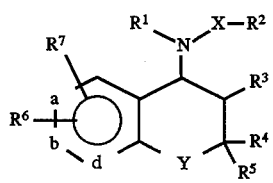

and pharmaceutically acceptable salts thereof which comprises converting a compound of the formula

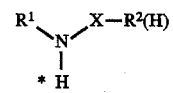

where the $R^2$ substituent contains a hydrogen atom which is more acidic than the starred (*) hydrogen atom in formula II, to the corresponding dianion of formula

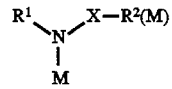

where M is a counterion preferably lithium or magnesium, using two equivalents of a base in an inert solvent such as tetrahydrofuran; then reacting compounds of formula IIA with an epoxide of formula

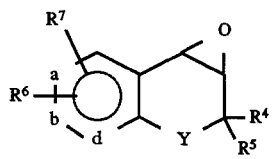

to produce the compounds of formula I.

15 Claims, No Drawings

U.S. PATENT DOCUMENTS

| | | | |
|---|---|---|---|
| 3,953,506 | 4/1976 | Spicer et al. | 260/553 |
| 4,238,501 | 12/1980 | Kabbe et al. | 424/283 |
| 4,251,537 | 2/1981 | Evans | 424/267 |
| 4,363,811 | 12/1982 | Evans et al. | 424/267 |
| 4,366,163 | 12/1982 | Evans et al. | 424/267 |
| 4,391,815 | 7/1983 | Evans | 424/274 |
| 4,428,881 | 1/1984 | Hedrich et al. | 548/491 |
| 4,481,213 | 11/1984 | Evans | 424/283 |
| 4,568,692 | 2/1986 | Evans | 514/456 |
| 4,571,406 | 2/1986 | Evans et al. | 514/456 |
| 4,575,511 | 3/1986 | Evans et al. | 514/456 |
| 4,602,022 | 7/1986 | Cozzi et al. | 514/337 |
| 4,659,737 | 4/1987 | Kabbe et al. | 514/456 |
| 4,687,779 | 8/1987 | Evans | 514/456 |
| 4,734,421 | 3/1988 | Hammond et al. | 514/274 |
| 4,772,603 | 9/1988 | Evans | 514/241 |
| 4,782,083 | 11/1988 | Cassidy et al. | 514/456 |
| 4,831,050 | 5/1989 | Cassidy et al. | 514/422 |
| 4,904,784 | 2/1990 | Evans et al. | 546/90 |
| 4,925,839 | 5/1990 | Quagliato et al. | 514/212 |
| 4,943,582 | 7/1990 | Evans et al. | 514/320 |
| 4,971,982 | 11/1990 | Attwod et al. | 514/337 |
| 4,988,723 | 1/1991 | Shiokawa et al. | 514/392 |
| 5,006,523 | 4/1991 | Atwal | 514/227.5 |
| 5,011,837 | 4/1991 | Atwal et al. | 514/227.8 |
| 5,013,853 | 5/1991 | Gericke et al. | 549/401 |
| 5,021,432 | 6/1991 | Yamanaka et al. | 514/337 |
| 5,028,711 | 7/1991 | Stenzel et al. | 546/196 |
| 5,053,427 | 10/1991 | Stemp et al. | 514/456 |
| 5,061,813 | 10/1991 | Atwal | 549/399 |
| 5,071,871 | 12/1991 | Blarer et al. | 514/456 |
| 5,082,858 | 1/1992 | Garcia et al. | 514/456 |
| 5,095,016 | 3/1992 | Ohtuka et al. | 514/233.5 |
| 5,096,914 | 3/1992 | Stenzel et al. | 514/392 |
| 5,104,890 | 4/1992 | Shiokawa et al. | 514/370 |
| 5,140,031 | 8/1992 | Atwal et al. | 514/302 |
| 5,143,924 | 9/1992 | Gericke et al. | 514/337 |
| 5,143,936 | 9/1992 | Yamanaka et al. | 514/456 |
| 5,145,985 | 9/1992 | Timar et al. | 548/525 |
| 5,210,234 | 5/1993 | Evans et al. | 549/398 |
| 5,238,937 | 8/1993 | Gericke et al. | 514/253 |
| 5,254,555 | 10/1993 | Stemp et al. | 514/256 |
| 5,268,386 | 12/1993 | Harada et al. | 514/456 |
| 5,276,168 | 1/1994 | Atwal | 549/404 |
| 5,278,169 | 1/1994 | Atwal | 514/302 |
| 5,286,753 | 2/1994 | Schaus et al. | 514/657 |
| 5,310,750 | 5/1994 | Berge et al. | 514/402 |
| 5,310,932 | 5/1994 | Atwal et al. | 548/454 |
| 5,317,029 | 5/1994 | Inazu et al. | 514/422 |
| 5,318,969 | 6/1994 | Yamanaka et al. | 514/247 |
| 5,374,643 | 12/1994 | Atwal et al. | 514/364 |
| 5,393,771 | 2/1995 | Atwal | 514/394 |
| 5,401,848 | 3/1995 | Atwal | 546/153 |

OTHER PUBLICATIONS

R. Albrecht et al., "Chemotherapeutic Nitroheterocycles. XI (1). Indanylamides and Indanylesters of 5–nitrofurancarboxylic Acids and Analogous Compounds as Antimicrobial Agents", *Chimie Therapeutique*, vol. 7, No. 1, pp. 9–13 (1972).

H. J. Petersen et al., "Synthesis and Hypotensive Activity of N–Alkyl–N"–cyano–N'–pyridylguanidines", *J. of Med. Chem.*, vol. 21, No. 8, pp. 773–781 (1978).

V. A. Ashwood et al., "Synethsis and Antihypertensive Activity of 4–(Cyclic amido)–2H–1–benzopyrans", *J. Med. Chem.*, 29, pp. 2194–2201 (1986).

C. R. Rasmussen et al., "Improved Procedures for the Preparation of Cycloalkyl–, Arylalkyl–, and Arythioureas", *Synthesis*, pp. 456–459 (1988).

V. V. Mozolis et al., "Preparation of N–Substituted Thiourea", *Russian Chem. Reviews*, 42(7), pp. 587–595 (1973).

J. M. Evans et al., "Synthesis and Antihypertensive Activity of Substituted trans–4–Amino–3,4–dihydro–2, 2–dimethy–2H–1–benzopyran–3–ols", *J. Med. Chem.*, 26, pp. 1582–1589 (1983).

R. W. Lang et al., "Synthesis of Selectively Trifluoromethylated Pyridine Derivatives as Potential Antihypertensives", *Helvetica Chimica Acta*, vol. 72, pp. 596–601 (1988).

P. Sebok et al., "Selective synthesis of Analogues of the Natural Precocenes, Synthesis and Regioselective (–Alkylation of 6–Chloro–and 6–Tert–Butyl–7,8–Dihyedroxy–2, 2–Dimethyl–4–Chromanones", *Heterocycles*, 217, pp. 2595–2607 (1988).

P. Teixidor et al., "Improved Preparation of Precocone II, Unexpected Results in the Reduction of Alkoxy Substituted Acetophenones and 4–Chromanones with Sodium Borohydride", *Heterocycles*, 27, pp. 2459–2465 (1988).

A. Banerji et al., "Enolates of O–Hydroxyacetophenones: Novel Synthesis of 2,2–Dialkyl–4–Chromanones", *Tetrahedrom Letters*, No. 38, pp. 2685–2686 (1979).

G. Ariamala et al., "A Simple Route for the Synthesis of 4–Chlorochromanes and Chroman–4–one", *Tetrahedrom Letters*, 29, No. 28, pp. 3487–3488 (1988).

G. A. Epling et al., "Efficient Alkylation of Nitrogen Heterocycles Using Lithium Salts and Oxygen Leaving Groups", *Synlett*, pp. 347–348 (1991).

PROCESS FOR PREPARING 4-ARYLAMINO-BENZOPYRAN AND RELATED COMPOUNDS

BRIEF DESCRIPTION OF THE INVENTION

The present invention is directed to a method of preparing compounds of the formula

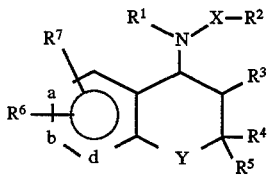    I and pharmaceutically acceptable salts thereof which comprises converting a compound of the formula

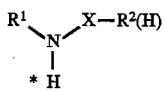    II where the $R^2$ substituent contains a hydrogen atom which is more acidic than the starred (*) hydrogen atom in formula II, to the corresponding dianion of formula

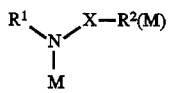    IIA where M is a counterion preferably lithium or magnesium, using two equivalents of a base in an inert solvent such as tetrahydrofuran.

Compounds of formula IIA are then reacted with an epoxide of formula

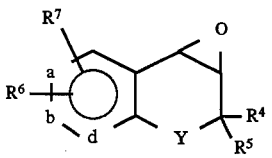    III to produce the compounds of formula I.

The invention also comprises the conversion of a compound of formula II where the $R^2$ substituent does not contain a hydrogen atom which is more acidic than the starred (*) hydrogen atom in formula II, to the corresponding monoanion using one equivalent of a base and subsequent reaction with III to produce the compounds of formula I.

As used in the above formulae, and throughout the specification, the symbols have the following meanings:

a, b and d are all carbon atoms or one of a, b and d is a nitrogen atom or —N(O)— and the others are carbon atoms;

Y is a single bond, —$CH_2$—, —C(O)—, —O—, —S— or —N($R^8$)—;

$R^1$ is aryl or heterocyclo;

$R^2$ is —$COR^8$, —CO—amino, —CO-substituted amino, amino, substituted amino, —$NR^8CO$—amino, —$NR^8CO$-substituted amino, —$NR^8COR^9$, —$NR^8SO_2R^9$, —$NR^8$(C=NCN)-amino —$NR^8$(C=NCN)-substituted amino.

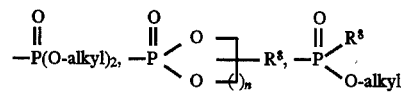

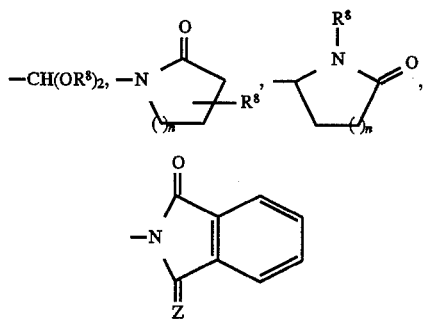

pyridine-N-oxide,
(where Z is O or $H_2$) or

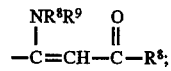

$R^3$ is hydroxy;

$R^4$ and $R^5$ are each independently hydrogen, alkyl or arylalkyl, or $R^4$ and $R^5$ taken together with the carbon atom to which they are attached form a 5- to 7-membered carbocyclic ring;

$R^6$ is hydrogen, alkyl, haloalkyl, alkenyl, alkynyl, cycloalkyl, arylalkyl, (cycloalkyl)alkyl, —CN, —$NO_2$, —$COR^8$, —$COOR^8$, —$CONHR^8$, —$CONR^8R^9$, —$CF_3$, —S-alkyl, —SOalkyl, —$SO_2$alkyl,

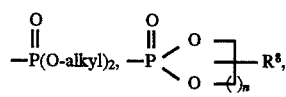

halogen, amino, substituted amino, —O-alkyl, —$OCF_3$, —$OCH_2CF_3$, —OCOalkyl, —$OCONR^8$alkyl, —$NR^8CO$-alkyl, —$NR^8COO$alkyl or —$NR^8CONR^9$, tetrazolyl, imidazole, oxazole, triazole or —$S(O)_2NR^{10}R^{11}$;

$R^7$ is hydrogen, alkyl, hydroxy, —O-alkyl, amino, substituted amino, —$NRCOR^8$, —CN or —$NO_2$; or when $R^6$ is —$S(O)_2NR^{10}R^{11}$, then $R^7$ may also be halogen, heterocyclo, haloalkyl or aryl;

$R^8$ and $R^9$ are independently hydrogen, alkyl, haloalkyl, aryl, arylalkyl, cycloalkyl or (cycloalkyl)alkyl;

$R^{10}$ and $R^{11}$ are independently hydrogen, alkyl, cycloalkyl, aryl, arylalkyl, haloalkyl, hydroxyalkyl, hydroxyalkyl substituted with a carboxylic ester or carboxylic acid, alkoxyalkyl, thioalkyl, (cycloalkyl) alkyl, morpholinylalkyl, heterocyclo or (heterocyclo) alkyl;

or $R^{10}$ and $R^{11}$ taken together with the nitrogen atom to which they are attached form a 5- to 7-membered mono or bicyclic ring, including fused rings such as 1-pyrrolidinyl, 1-piperidinyl, 1-azepinyl, 4-morpholinyl, 4-thiamorpholinyl, 4-thiamorpholine dioxide, 1-piperazinyl, 4-alkyl-1-piperazinyl, 4-arylalkyl-1-piperazinyl, 4-diarylalkyl-1-piperazinyl; or 1-piperazinyl, 1-pyrrolidinyl, 1-piperidinyl or 1-azepinyl substituted with one or more alkyl, alkoxy, alylthio, halo, trifluoromethyl, hydroxy, aryl, arylalkyl, —COOR$^8$ or —CO-substituted amino;

or R$^{10}$ and R$^7$ taken together with the atoms to which they are attached form a 5- to 7-membered ring optionally substituted with aryl;

X is alkyl; or X—R$^2$ together can be hydrogen, aryl or heterocycle when R$^1$ is heterocyclo; and n is an integer of 1 to 3.

The compounds of this invention possess antiischemic activity and are useful, for example as cardiovascular agents.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group).

The term "alkyl" refers to both straight and branched chain groups having 1 to 8 carbon atoms preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups optionally substituted with one or more substituents selected from halogen, alkoxy, aryl, alkylaryl, haloaryl, cycloalkyl, (cycloalkyl)alkyl, hydroxy, alkylamine, alkyl-substituted amino, alkanoylamino, arylcarbonylamino, nitro, cyano, thiol, alkylthio or —COOR$^8$.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups having at least 2 carbon atoms further containing at least one carbon to carbon double bond.

The term "alkynyl" refers to any of the above alkyl groups having at least 2 carbon atoms further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl; phenyl, 1-naphthyl, 2-naphthyl, mono-substituted with ($C_1$–$C_4$)-alkyl, ($C_1$–$C_4$)-alkylthio, ($C_1$–$C_4$)-alkoxy, halo, nitro, cyano, hydroxy, amino, (alkyl)amino, alkyl-substituted amino, —NH—($C_1$–$C_4$)-alkyl, —N(($C_1$–$C_4$)-alkyl), —CF$_3$, —OCHF$_2$,

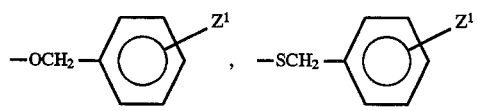

(where $Z^1$ is hydrogen, ($C_1$–$C_4$)-alkyl, ($C_1$–$C_4$)-alkylthio ($C_1$–$C_4$)-alkoxy, halo, hydroxy or —CF$_3$), —O—CH$_2$-cycloalkyl, or —S—CH$_2$-cycloalkyl; and phenyl, 1-naphthyl or 2-naphthyl, di-substituted with methyl, methoxy, methylthio, halo, —CF$_3$, nitro, amino, —OCHF$_2$, carboxylic acid or carboxylic ester. The term "aryl" also includes those groups listed above fused to a five- or six-membered ring which optionally contains an O, S or N atom (the nitrogen atom being substituted by an R$^7$ group). referred aryl groups include unsubstituted phenyl and mono-substituted phenyl wherein the substituents are ($C_1$–$C_4$)-alkyl, methoxy, halo, nitro, cyano or —CF$_3$.

The term "heterocyclo" or "hetero" refers to fully saturated or unsaturated rings of 5 or 6 atoms containing one or two oxygen and/or sulfur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl and imidazolyl. The term "hetero" also includes bicyclic rings wherein the five- or six-membered ring containing oxygen and/or sulfur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term "heterocyclo" or "hereto" also includes such monocyclic and bicyclic rings wherein an available carbon atom is substituted with a ($C_1$–$C_4$)-alkyl, aryl, ($C_1$–$C_4$)-alkylthio, ($C_1$–$C_4$)-alkoxy, halo, nitro, keto, cyano, hydroxy, azo, thiazo, amino, —NH—($C_1$–$C_4$)-alkyl, —N(($C_1$–$C_4$)-alkyl)$_2$, —CF$_3$, (aminoester)alkyl, carboxylic acid, carboxylic ester, —OCHF$_2$ or ($C_1$–$C_4$)-alkoxy further substituted with a carboxylic acid or such monocyclic and bicyclic rings wherein two or three available carbons have substituents selected from methyl, methoxy, methylthio, halo, —CF$_3$, nitro, hydroxy, amino and —OCHF$_2$.

The term "substituted amino" refers to a group of the formula —NZ$^2$Z$^3$ wherein Z$^2$ is hydrogen, alkyl, cycloalkyl, aryl, arylalkyl, (cycloalkyl)alkyl, morpholinylalkyl, heterocyclo or (heterocyclo)alkyl and Z$^3$ is hydrogen, alky, cycloalkyl, aryl, arylalkyl, haloalkyl, hydroxyalkyl, alkoxyalkyl, thioalkyl, (cycloalkyl)alkyl or hydroxyalkyl further substituted with a carboxylic ester or carboxylic acid, with the proviso that when Z$^2$ is hydrogen, then Z$^3$ is other than hydrogen; or Z$^2$ and Z$^3$ taken together with the nitrogen atom to which they are attached are 1-pyrrolidinyl, 1-piperidinyl, 1-azepinyl, 4-morpholinyl, 4-thiamorpholinyl, 1-piperidinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phospshoric acid or a hydrohalic acid, with organic carboxylic acids, such as alkanecarboxylic acids of 1 to 4 carbon atoms which are unsubstituted or substituted, (for example, by halogen), for example acetic acid, such as saturated or unsaturated dicarboxylic acids, for example oxalic, malonic, succinic, maleic, fumaric, phthalic or terphthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$)-alkyl- or ($C_1$–$C_4$)-substituted alkyl- or aryl-sulfonic acids which are unsubstituted or substituted, (for example by halogen), for example methane-, p-toluene-sulfonic, 2-hydroxy ethanesulfonic or 1,2-bis ethanesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl- diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of formula I are contemplated, either in admixture or in pure or substantially pure form. The compounds of formula I can have asymmetric centers at any of the carbon atoms including any one of the R substituents. Consequently, compounds of formula I can exist in diastereomeric forms or in mixtures thereof. When diastereomeric products are prepared, they can be separated by conventional methods for example, chromatographic or fractional crystallization.

The compounds of formula I may, for example, be in the free or hydrate form, and may be obtained by methods exemplified by the following description.

The invention comprises the conversion of a compound of the formula

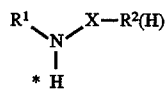  II where the $R^2$ substituent contains a hydrogen atom which is more acidic than the starred (*) hydrogen atom in formula II, to the corresponding dianion of formula

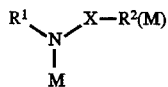  IIA where M is a counterion preferably lithium or magnesium, using two equivalents of a base in an inert solvent such as tetrahydrofuran. Examples of suitable bases are alkyl or aryl lithium reagents (for example, n-butyl lithium), lithium hydride, lithium amide bases (for example lithium diisopropyl amide or preferably lithium bis(trimethylsilyl)amide (LiHMDS)), and alkyl or aryl Grignard reagents (such as ethylmagnesium bromide or ethylmagnesium chloride).

Compounds of formula IIA are then reacted with an epoxide of formula

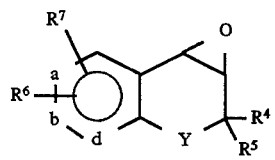  III to produce the compounds of formula I.

The invention also comprises the conversion of a compound of formula II where the $R^2$ substituent does not contain a hydrogen atom which is more acidic than the starred (*) hydrogen atom in formula II, to the corresponding monoanion using one equivalent of the above listed bases and subsequent reaction with III to produce the compounds of formula I.

As known by those having ordinary skill in the art, where the substituent $R^1$, $R_6$ or $R^7$ contains an acidic group, for example when $R^7$ is hydroxy, one additional equivalent of a base will be necessary.

Compounds of the formula II are prepared by reductive amination of an amine of formula IV

with an aldehyde of formula V

in the presence of a reducing agent such as sodium borohydride, sodium cyanoborohydride and sodium triacetoxyborohydride. Compounds of formula IV and V are commercially available or they can be prepared by standard methods described in textbooks of organic chemistry such as Introduction to Organic Chemistry by A. Streitwieser and C. H. Heathcock, Macmillan Publishing Co., Inc. N.Y. (1976) and Advanced Organic Chemistry by F. C. Carey and R. J. Sundberg, Plenum Publishing Co., N.Y. (1977).

Compounds of formula III wherein Y is a single bond can be prepared according to D. R. Buckle, et al., *J. Med. Chem.*, 34, 919 (1991).

Compounds of formula III wherein Y is —$CH_2$— can be prepared by methods described in V. A. Ashwood, et al., *J. Med. Chem.*, 34, 3261 (1991).

Compounds of formula III where Y is —C(O)— can be prepared by methods described by C. Almansa et al., *J. Med. Chem.*, vol. 36, p. 2121–2133 (1993).

Compounds of formula III where Y is —O—, can be prepared by methods described in the literature, such as by J. M. Evans, et al., *J. Med. Chem.*, 26, 1582 (1983); J. M. Evans, et al., *J. Med. Chem.*, 29, 2194(1986); R. W. Lang et al., *Helvetica Chimica Acsta*, 71, 596(1988); European patent 0205292 A2 and PCT patent 87/07607.

Compounds of formula III where Y is —S— can be prepared according to methods described by D. Smith et al., EP-0322251.

Compounds of formula III where Y is —N($R^8$)— can be prepared according to D. R. Buckle, et al., *J. Med. Chem.*, 34, 919(1991) and PCT patent 85/050083.

To prepare enantiomers of epoxide III, an olefin of formula IV

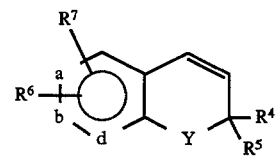  formula IV is epoxidized with an oxidizing agent such as commercial bleach using a metal catalyst such as chiral manganese catalyst of the formula

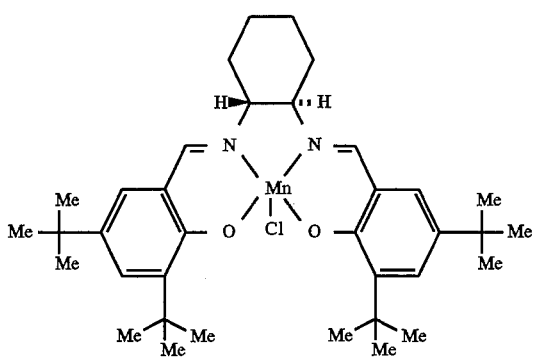

as described by N. H. Lee, et al. *Tetrahedron Letters*, 32, 5055–5058 (1991), to provide predominantly the chiral expoxide of formula

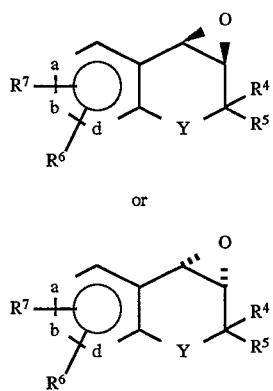

depending on the chirality of the 1,2-diaminocyclohexane used in the preparation of a compound of formula V as described by Lee et al. The epoxides of formulae IIIA and IIIB can then be utilized to prepare the chiral compounds of formula I.

The olefins of formula IV wherein Y is —O— can be prepared according to *Tetrahedron Letters*, 35, p. 6405–6408 (1994) and references cited therein.

Compounds of formula IV wherein Y is a single bond or —N($R^8$)— can be prepared according to D. R. Buckle, et al., *J. Med. Chem.*, 34, p. 919 (1991).

Compounds of formula IV wherein Y is —$CH_2$—can be prepared by methods described in V. A. Ashwood, et al., *J. Med. Chem.*, 34, p. 3261 (1991).

Compounds of formula IV wherein Y is —C(O)— may be prepared by methods described by C. Almansa et al., *J. Med. Chem.*, Vol. 36, p. 2121–2133 (1993).

Compounds of formula IV wherein Y is —S— can be prepared according to the methods described by D. Smith et al., EP-0322251.

If any of the R substituents, X or Y groups contain reactive groups such as hydroxy or amino that can interfere with the epoxide opening reaction or any other reactions, they should be protected with appropriate protecting groups.

The compounds prepared by the method disclosed herein can have asymmetric centers at carbons 2–4 of the bicyclic ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The process of the present invention may be utilized to prepare the following preferred compounds of formula I where:

a, b and d are carbon atoms;
X is alkyl;
Y is a single bond or —O—;
$R^1$ is aryl or heterocyclo;
$R^2$ is —$COOR^8$, —CO-amino, —CO-substituted amino, —$NHCOCH_3$, —$NHSO_2Me$, —$NHCONH_2$, —NH(C=NCN)$NH_2$, imidazole, furan, pyridine, oxazole, hydroxy, —NHCO-substituted amino or —$SO_2Me$;
$R^3$ is hydroxy;
$R^4$ and $R^5$ are methyl;
$R^6$ is cyano, —$NO_2$, —$CF_3$, halo, alkyl, tetrazol or —$S(O)_2NR^{10}R^{11}$;
$R^7$ is hydrogen;
or $R^{10}$ and $R^7$ taken together with the atoms to which they are attached form a 5- to 7-membered ring optionally substituted with aryl.

Compounds of formula I having predominantly trans stereochemistry may be prepared by preferably forming the corresponding mono or di-lithium derivatives using the bases described herein. Compounds of formula I having predominantly cis stereochemistry may be prepared by preferably forming the corresponding mono or di-magnesium derivatives using the Grignard reagents described herein.

Compounds of formula I may be used as antiischemic agents, i.e., for the treatment of ischemic conditions such as myocardial ischemia, cerebral ischemia, lower limb ischemia and the like.

Thus a composition containing one (or a combination of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of the compounds of formula I, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, and in limiting myocardial infarction.

Compounds of the formula I are additionally expected to be useful in the treatment of central nervous system disorders (e.g. Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatment of male impotence, as well as for the promotion of hair growth (e.g., in the treatment of male pattern baldness), and as anti-asthmatic agents.

The compounds of the formula I can also be formulated in combination with a diuretic such as chlorothiazide, hydrochlorothiazide, flumethiazide, hydroflumethiazide, bendroflumenthiazide, methylchlothiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant TPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

(3R-trans)-4-[4-Chloro-N-(1H-imidazol-2-ylmethyl) phenylamino]-3,4-dihydro-3-hydroxy-2,2-dimethyl-2H-1-benzopyran-6-carbonitrile

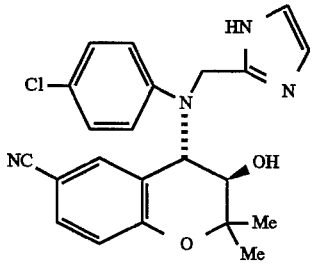

A. N-(4-Chlorophenyl)-N-[(1H-imidazol-2yl)methyl]-amine

In a 3-L flask equipped with a mechanical stirrer, internal temperature probe and reflux condenser, a mixture of 4-chloroaniline (100.00 g, 0.78 mol) and 2-imidazolecarboxaldehyde in methanol (1500 mL) was stirred at 60° C. under argon overnight. The heterogeneous mixture became homogeneous after one hour. The reaction mixture was allowed to cool to room temperature and then cooled to 5° C. in an ice/water bath. Portion wise addition of $NaBH_4$ (32.62 g, 0.86 mol) was begun. As the first half of the $NaBH_4$ was added over 20 min, the internal temperature rose gradually to 22° C. As the remaining $NaBH_4$ was added, the temperature dropped gradually to 10° C. The reaction mixture was allowed to warm to room temperature over 2 h and then stirred for an additional 1 h. The reaction mixture was concentrated in vacua to ~750 mL and then heated to 50° C. Water (1500 mL) was added dropwise. The resulting slurry was stirred at 45° C. for 30 min, allowed to cool to room temperature, and stirred overnight. The product was collected by filtration, washed with 1:2 methanol:water (first wash 100 mL, second wash 200 mL), air-dried for 7 h and then dried under high vacuum overnight to afford the title compound as a light yellow crystalline solid (140.5 g, 86%).

B. (1aR-cis)-1a,7b-Dihydro-2,2-dimethyl-2H-oxireno-[c][1]benzopyran-6-carbonitrile The title compound was prepared by the procedure described by Lee et al., Tetrahedron Letters, 32, 5055 (1991).

C. (3R-trans)-4-[4-Chloro-N-(1H-imidazol-2-ylmethyl) phenylamino]-3,4-dihydro-3-hydroxy-2,2-dimethyl-2H-1-benzopyran-6-carbonitrile.

A clear, yellow solution of the title A compound (36.34 g, 175 mmol) in distilled THF (530 mL) was stirred using a mechanical stirrer, under an argon atmosphere, and cooled to 0° C. (internal temperature). Lithium bis(trimethylsilyl) amide (350 mL of a 1.0M solution in THF, 350 mmol) was added slowly over 45 min (internal temperature maintained at 0° to 2° C.). After stirring an additional 45 min at 0° C., a solution of the title B compound (33.45 g, 166 mmol) in distilled THF (250 mL) was cannulated into the clear, brown dianion solution over a period of 17 min (no exotherm detected). The flask was rinsed with THF (2×10 mL) to complete the transfer of epoxide and the rinsings were added to the reaction flask. After stirring at 0° C. for 4.5 h (~94% conversion by HPLC), the reaction vessel was transferred to the cold room (5° C.) where it stood undisturbed for 16 h. The clear, brown solution was cooled to 0° C. and quenched by adding 1N HCl (350 mL) in one portion. The mixture, now at 27° C., was stirred at room temperature (15 min) and the THF was removed in vacuo to obtain an off-white solid and a clear aqueous layer. Ethyl acetate (900 mL) was added and the mixture still containing undissolved solids was transferred to a separatory funnel. After the pH of the aqueous phase containing the insoluble material was lowered from 3.6 to 1.2 with conc HCl (~10 mL), ethyl acetate (75 mL) and water (50 mL) were added to produce a clear, biphasic mixture. It was necessary to keep the pH of the aq layer ~1 to prevent precipitation of the free base. After mixing vigorously, the phases were separated and the aqueous fraction was back-extracted with ethyl acetate (2×125 mL). The combined organic extracts were washed with 1N HCl (350 mL), 50% aq sat sodium carbonate (4×350 mL), brine (150 mL), dried ($MgSO_4$) and filtered.

The clear, golden solution was partially concentrated in vacuo until the solution turned cloudy (450 g, ~5 mL ethyl acetate/theoretical g output of the title compound) and stirred for 0.5 h at 40° C. Hexanes (400 mL) were added with stirring over 2 min and the slurry was stirred for 1 h at room temperature. The white crystals were isolated by filtration, washed with hexanes (400 mL) and dried in vacuo to yield the title compound (61.38 g, 90%).

EXAMPLE 2

(3R-cis)-4-[4-Chloro-N-(1H-imidazole-2-ylmethyl)
phenylamino]-3,4-dihydro-3-hydroxy-2,2-dimethyl-
2H-1-benzopyran-6-carbonitrile

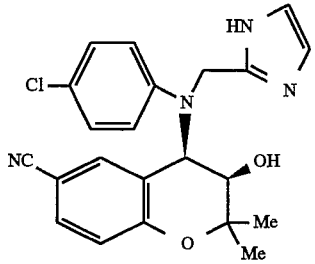

In a 50-mL flask equipped with argon inlet, internal temperature probe, and magnetic stir bar, the title A compound of Example 1 (0.762 g, 3.67 mmol) was dissolved in dry THF (7.50 mL) and cooled to 0° C. Ethyl magnesium bromide (7.70 mL of a 1M THF solution) was added dropwise via syringe over ten minutes while maintaining the internal temperature at ≦15° C. The reaction was cooled to 0° C. and the title B compound of Example 1 (0.738 g, 3.67 mmol) was added in one portion. The reaction was stirred for 14 h, quenched with 1N HCl (25 mL), and then diluted with ethyl acetate (50 mL). The layers were then separated and the aqueous layer was extracted with ethyl acetate (1×15 mL). The combined organic layers were washed with 1N HCl (1×25 mL), saturated aqueous NaHCO$_3$ (1×25 mL), saturated aqueous NaCl (1×25 mL), dried (MgSO$_4$), filtered, and concentrated to a white solid (1.53 g, 102%). Methanol (5 mL) and ethyl acetate (20 mL) were added to the solid producing a slurry which was heated to 56° C. while stirring. Additional methanol (0.5 mL) was added to form a clear, yellow solution. The solution was allowed to cool to ambient temperature and hexane (3 mL) was added to the solution. The resulting slurry was stirred overnight, filtered, and the filtrate washed with hexane (10 mL) to give the title compound as a white solid (0.766 g, 51%).

EXAMPLE 3

(3R-trans)-4-[4-Chloro-N-(1H-imidazole-2ylmethyl)
phenylamino]-3,4-dihydro-3-hydroxy-2,2-dimethyl-
2H-1-benzopyran-6-carbonitrile, HCl salt The title compound of Example 1 (117.695 g, 0.287 moles) was batched into a 2-liter, 3-necked flask equipped with a short path distillation apparatus, mechanical stirrer and thermocouple. Acetone (260 mL) was added to give a creamy white slurry. A 3N HCl solution (590 mL) was added to the acetone mixture with stirring. A slight exotherm was observed from 24° C. to 35° C. giving a cloudy solution. The mixture upon heating afforded a homogenous pale yellow solution. Acetone (140 mL) was distilled out of the acetone/ aqueous-acid solution. The reaction was cooled slowly to room temperature (~10° C. drop/hour) with seeding at 70° C. Large crystals were observed at 61° C. The slurry was allowed to stir overnight at 25° C. The white colored material was filtered at 25° C. and was washed with 150 mls of acidic water (pH=2). The white material was dried in a vacuum oven overnight (35° C.) to yield the title compound as a white crystalline solid (119.405 g, 93.2M %)

EXAMPLE 4

(3S-trans)-4-[(4-Chlorophenyl)(1H-imidazol-2-
ylmethyl)-amino]-3,4-dihydro-3-hydroxy-2,2-
dimethyl-N,N-bis(2-methylpropyl)-2H-1-
benzopyran-6-sulfonamide

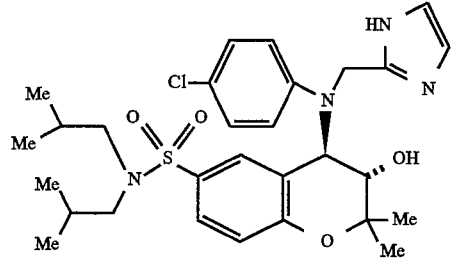

A. (1aS-cis)-1-[(1a,7b-dihydro-2,2-dimethyl-2,2-dimethyl-
2H-oxireno[1][c]benzopyran-6-yl)-N,N-bis(2-
methylpropyl)sulfonamide

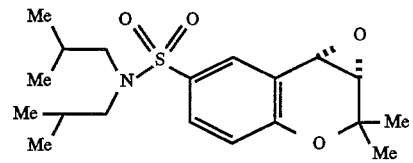

The title compound was prepared from the corresponding olefin by the procedure of Lee et al, Tetrahedron Letters, 32, 5055 (1991).

B. (3S-trans)-4-[4-Chlorophenyl)(1H-imidazole-2-ylmethyl)-amino]-3,4-dihydro-3-hydroxy-2,2-dimethyl-N, N-bis(2-methylpropyl)-2H-1-benzopyran-6-sulfonamide A solution of the N-(4-chlorophenyl-N-[(1H-imidazol-2-yl)methyl]amine (445 mg, 2.14 mmol, the title A compound of Example 1) in dry THF (2.5 mL), was cooled to −78° C. and treated with 2.5M n-butyllithium in hexanes (1.7 ml, 4.28 mmol). The solution was allowed to warm to −25° C. and stirred for 0.5 hours then cooled back to −78° C. A solution of the title A compound (785 mg, 2.14 mmol) in THF was added via syringe. The solution was stirred overnight under argon while warming to room temperature. The solution was partitioned between ethyl acetate and (sat.aq.) NaHCO$_3$ solution. The organic fraction was washed with brine, dried over MgSO$_4$, filtered and solvent was removed in vacuo to give a brown gum. The residue was purified on silica gel using 40:60/ethyl acetate:hexane to give the title compound as a white solid (254 mg, 21%), mp 214°–216° C. (discoloration @ 185° C.). [α]$_D$=−37.5°, (c=0.64, MeOH). Analysis calculated for C$_{29}$H$_{39}$ClN$_4$O$_4$S: C, 60.56, H, 6,83, N, 9.74, Cl, 6.16, S, 5.57. Found C, 60.46, H, 6.93, N, 9.51, Cl, 5,87, S, 5.55.

What is claimed is:

1. A process for preparing compounds of formula

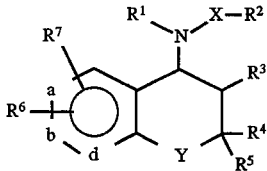

or pharmaceutically acceptable salts thereof wherein a, b and d are all carbon atoms or one of a, b and d is a nitrogen atom or —N(O)— and the others are carbon atoms;

Y is a single bond, —CH$_2$—, —C(O)—, —O—, —S— or —N(R$^8$)—;

R$^1$ is aryl or heterocyclo;

R$^2$ is —COOR$^8$, —CO-amino, —CO-substituted amino, amino, substituted amino, —NR$^8$CO-amino, —NR$^8$CO-substituted amino, —NR$^8$COR$^9$, —NR$^8$SO$_2$R$^9$, —NR$^8$(C=NCN)-amino, —NR$^8$(C=NCN)-substituted amino,

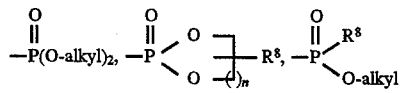

—SR$^8$, —SOR$^8$, —SO$_2$R$^8$, —OR$^{8'}$, cyano, heterocyclo, pyridine-N-oxide,

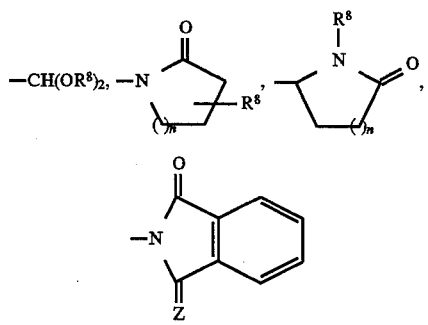

(where Z is O or H$_2$) or

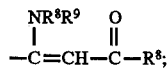

R$^2$ is hydroxy;

R$^4$ and R$^5$ are each independently hydrogen, alkyl or arylalkyl, or R$^4$ and R$^5$ taken together with the carbon atom to which they are attached form a 5- to 7-membered carbocyclic ring;

R$^6$ is hydrogen, alkyl, haloalkyl, alkenyl, alkynyl, cycloalkyl, arylalkyl, (cycloalkyl)alkyl, —CN, —NO$_2$, —COR$^8$, —COOR$^8$, —CONHR$^8$, —CONR$^8$R$^9$, —CF$_3$, —S-alkyl, —SOalkyl, —SO$_2$alkyl,

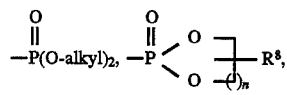

halogen, amino substituted amino, —O-alkyl, —OCF$_3$, —OCH$_2$CF$_3$, —OCOalkyl, —OCONR$^8$alkyl, —NR$^8$COalkyl, —NR$^8$COOalkyl or —NR$^8$CONR$^9$, tetrazolyl, imidazole, oxazole, triazole or —S(O)$_2$NR$^{10}$R$^{11}$;

R$^7$ is hydrogen, alkyl, hydroxy, —O-alkyl, amino, substituted amino, —NHCOR$^8$, —CN or —NO$_2$; or when R$^6$ is —S(O)$_2$NR$^{10}$R$^{11}$, then R$^7$ in addition to the above is halogen, heterocyclo, haloalkyl or aryl;

R$^8$ and R$^9$ are independently hydrogen, alkyl, haloalkyl, aryl, arylalkyl, cycloalkyl or (cycloalkyl)alkyl;

R$^{10}$ and R$^{11}$ are independently hydrogen, alkyl, cycloalkyl, aryl, arylalkyl, haloalkyl, hydroxyalkyl, hydroxyalkyl substituted with a carboxylic ester or carboxylic acid, alkoxyalkyl, thioalkyl (cycloalkyl) alkyl, morpholinylalkyl, heterocyclo or (heterocyclo) alkyl;

or R$^{10}$ and R$^{11}$ taken together with the nitrogen atom to which they are attached form a 5- to 7-membered mono or bicyclic ring, or 1-pyrrolidinyl, 1-piperidinyl, 1-azepinyl, 4-morpholinyl, 4-thiamorpholinyl, 4-thiamorpholine dioxide, 1-piperazinyl, 4-alkyl-1-piperazinyl, 4-arylalkyl-1-piperazinyl, 4-diarylalkyl-1-piperazinyl; or 1-piperazinyl, 1-pyrrolidinyl, 1-piperidinyl or 1-azepinyl substituted with one or more alkyl, alkoxy, alkylthio, halo, trifluoromethyl, hydroxy, aryl, arylalkyl, —COOR$^8$ or —CO-substituted amino;

or R$^{10}$ and R$^7$ taken together with the atoms to which they are attached form an unsubstituted 5- to 7-membered ring or a 5- to 7-membered ring substituted with aryl;

X is alkyl; or X—R$^2$ together are hydrogen, aryl or heterocyclo when R$^1$ is heterocyclo; and n is an integer of 1 to 3;

which comprises the steps of treating a compound of the formula

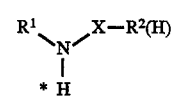 II (where the R$^2$ substituent contains a hydrogen atom which is more acidic than the starred (*) hydrogen atom in formula II); with two equivalents of a base in an inert solvent, to form the corresponding dianion of formula

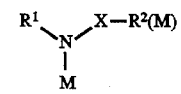 IIA where M is a counterion, then reacting the compounds of formula IIA with an epoxide of formula

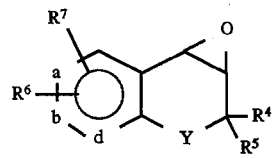 III to produce the compounds of formula I.

2. A process for preparing compounds of formula

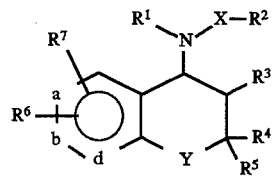 I or pharmaceutically acceptable salts thereof wherein a, b and d are all carbon atoms or one of a, b and d is a nitrogen atom or —N(O)— and the others are carbon atoms;

Y is a single bond, —CH$_2$—, —C(O)—, —O—, —S—O or —N(R$^8$)—;

R$^1$ is aryl or heterocyclo;

R$^2$ is —COOR$^8$, —CO-amino, —CO-substituted amino, amino, substituted amino, —NR$^8$CO-amino, —NR$^8$CO-substituted amino, —NR$^8$COR$^9$, —NR$^8$SO$_2$R$^9$, —NR$^8$(C=NCN)-amino, —NR$^8$(C=NCN)-substituted amino,

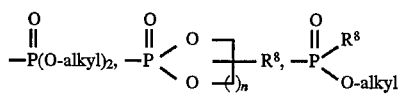

—SR⁸, —SOR⁸, —SO₂R⁸, —OR⁸, cyano, heterocyclo, pyridine-N-oxide,

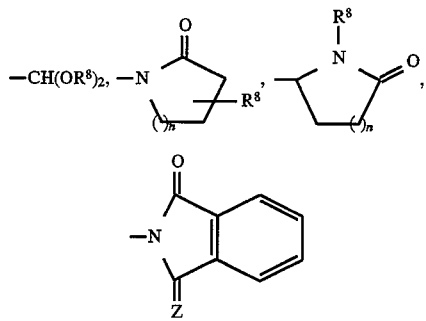

(where Z is O or H₂) or $$-\overset{NR^8R^9}{C}=CH-\overset{O}{\overset{\|}{C}}-R^8;$$

R³ is hydroxy;

R⁴ and R⁵ are each independently hydrogen, alkyl or arylalkyl, or R⁴ and R⁵ taken together with the carbon atom to which they are attached from a 5- to 7-membered carbocyclic ring;

R⁶ is hydrogen, alkyl, haloalkyl, alkenyl, alkynyl, cycloalkyl, arylalkyl, (cycloalkyl)alkyl, —CN, —NO₂, —COR⁸, —COOR⁸, —CONHR⁸, —CONR⁸R⁹, —CF₃, —S-alkyl, —SOalkyl, —SO₂alkyl,

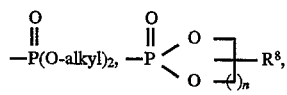

halogen, amino, substituted amino, —O-alkyl, —OCF₃, —OCH₂CF₃, —OCOalkyl, —OCONR⁸alkyl, —NR⁸COalkyl, —NR⁸COOalkyl or —NR⁸CONR⁹, tetrazolyl, imidazole, oxazole, triazole or —S(O)₂NR¹⁰R¹¹;

R⁷ is hydrogen, alkyl, hydroxy, —O-alkyl, amino, substituted amino, —NHCOR⁸, —CN or —NO₂; or when R⁶ is —S(O)₂NR¹⁰R¹¹, then R⁷ is also halogen, heterocyclo, haloalkyl or aryl;

R⁸ and R⁹ are independently hydrogen, alkyl, haloalkyl, aryl, arylalkyl, cycloalkyl or (cycloalkyl)alkyl;

R¹⁰ and R¹¹ are independently hydrogen, alkyl, cycloalkyl, aryl, arylalkyl, haloalkyl, hydroxyalkyl, hydroxyalkyl substituted with a carboxylic ester or carboxylic acid, alkoxyalkyl, thioalkyl, (cycloalkyl) alkyl, morpholinylalkyl, heterocyclo or (heterocyclo) alkyl;

or R¹⁰ and R¹¹ taken together with the nitrogen atom to which they are attached form a 5- to 7-membered mono or bicyclic ring, or 1-pyrrolidinyl, 1-piperidinyl, 1-azepinyl, 4-morpholinyl, 4-thiamorpholinyl, 4-thiamorpholine dioxide, 1-piperazinyl, 4-alkyl-1-piperazinyl, 4-arylalkyl-1-piperazinyl, 4-diarylalkyl-1-piperazinyl; or 1-piperazinyl, 1-pyrrolidinyl, 1-piperidinyl or 1-azepinyl substituted with one or more alkyl, alkoxy, alylthio, halo, trifluoromethyl, hydroxy, aryl, arylalkyl, —COOR⁸ or —CO-substituted amino;

or R¹⁰ and R⁷ taken together with the atoms to which they are attached form an unsubstituted 5- to 7-membered ring or a 5- to 7-membered ring substituted with aryl;

X is alkyl; or X—R² together are hydrogen, aryl or heterocyclo when R¹ is heterocyclo; and n is an integer of 1 to 3;

which comprises the steps of treating a compound of the formula

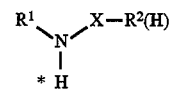

(where the R² substituent does not contain a hydrogen atom which is more acidic than the starred (*) hydrogen atom in formula II); with one equivalent of a base in an inert solvent, to form the corresponding monoanion, then reacting the monoanion with an epoxide of formula

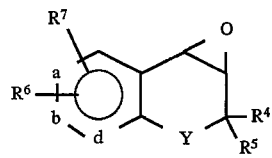

to produce the compounds of formula I.

3. The process of claim 1 wherein the base is an alkyl or aryl lithium or a lithium amide base.

4. The process of claim 3 wherein the base is n-butyl lithium, lithium diisopropylamide or lithium bis (trimethylsilyl)amide.

5. The process of claim 1 wherein the base is a Grignard reagent.

6. The process of claim 5 wherein the Grignard reagent is ethylmagnesium bromide or ethylmagnesium chloride.

7. The process of claim 1 wherein compounds of formula I are prepared where a, b and d are carbon atoms;

X is alkyl;

Y is a single bond or —O—;

R¹ is aryl or heterocyclo;

R² is —COOR⁸, —CO-amino, —CO-substituted amino, —NHCOCH₃, —NHSO₂Me, —NHCONH₂, —NH (C=NCN)NH₂, imidazole, furan, pyridine, oxazole, hydroxy, —NHCO-substituted amino or —SO₂Me;

R³ is hydroxy;

R⁴ and R⁵ are methyl;

R⁶ is cyano, —NO₂, —CF₃, halo, alkyl, tetrazol or —S(O)₂NR¹⁰R¹¹;

R⁷ is hydrogen;

or R¹⁰ and R⁷ taken together with the atoms to which they are attached form an unsubstituted 5- to 7-membered ring or a 5- to 7-membered ring substituted with aryl.

8. The process of claim 4 wherein compounds of formula I are prepared where a, b and d are carbon atoms;

X is alkyl;

Y is a single bond or —O—;

R¹ is aryl or heterocyclo;

R² is —COOR⁸, —CO-amino, —CO-substituted amino, —NHCOCH₃, —NHSO₂Me, —NHCONH₂, —NH (C=NCN)NH₂, imidazole, furan, pyridine, oxazole, hydroxy, —NHCO-substituted amino or —SO₂Me;

$R^3$ hydroxy;

$R^4$ and $R^5$ are methyl;

$R^6$ is cyano, —$NO_2$, —$CF_3$, halo, alkyl, tetrazol or —$S(O)_2NR^{10}R^{11}$;

$R^7$ is hydrogen;

or $R^{10}$ and $R^7$ taken together with the atoms to which they are attached form an unsubstituted 5- to 7-membered ring or a 5- to 7-membered ring substituted with aryl.

9. The process of claim 2 wherein the base is an alkyl or aryl lithium or a lithium amide base.

10. The process of claim 9 wherein the base is n-butyl lithium, lithium diisopropylamide or lithium bis (trimethylsilyl)amide.

11. The process of claim 2 wherein the base is a Grignard reagent.

12. The process of claim 11 wherein the Grignard reagent is ethylmagnesium bromide or ethylmagnesium chloride.

13. The process of claim 2 wherein compounds of formula I are prepared where a, b and d are carbon atoms;

X is alkyl;

Y is a single bond or —O—;

$R^1$ is aryl or heterocyclo;

$R^2$ is —$COOR^8$, —CO-amino, —CO-substituted amino, —$NHCOCH_3$, —$NHSO_2Me$, —$NHCONH_2$, —NH(C=NCN)$NH_2$, imidazole, furan, pyridine, oxazole, hydroxy, —NHCO-substituted amino or —$SO_2Me$;

$R^3$ is hydroxy;

$R^4$ and $R^5$ are methyl;

$R^6$ is cyano, —$NO_2$, —$CF_3$, halo, alkyl, tetrazol or —$S(O)_2NR^{10}R^{11}$;

$R^7$ is hydrogen;

or $R^{10}$ and $R^7$ taken together with the atoms to which they are attached form an unsubstituted 5- to 7-membered ring or a 5- to 7-membered ring substituted with aryl.

14. The process of claim 10 wherein compounds of formula I are prepared where a, b and d are carbon atoms;

X is alkyl;

Y is a single bond or —O—;

$R^1$ is aryl or heterocyclo;

$R^2$ is —$COOR^8$, —CO-amino, —CO-substituted amino, —$NHCOCH_3$, —$NHSO_2Me$, —$NHCONH_2$, —NH(C=NCN)$NH_2$, imidazole, furan pyridine, oxazole, hydroxy, —NHCO-substituted amino or —$SO_2Me$;

$R^3$ is hydroxy;

$R^4$ and $R^5$ are methyl;

$R^6$ is cyano, —$NO_2$, —$CF_3$, halo, alkyl, tetrazol or —$S(O)_2NR^{10}R^{11}$;

$R^7$ is hydrogen;

or $R^{10}$ and $R^7$ taken together with the atoms to which they are attached form an unsubstituted 5- to 7-membered ring or a 5- to 7-membered ring substituted with aryl.

15. The process of claim 12 wherein compounds of formula I are prepared where a, b and d are carbon atoms;

X is alkyl;

Y is a single bond or —O—;

$R^1$ is aryl or heterocyclo;

$R^2$ is —$COOR^8$, —CO-amino, —CO-substituted amino, —$NHCOCH_3$, —$NHSO_2Me$, —$NHCONH_2$, —NH(C=NCN)$NH_2$, imidazole, furan, pyridine, oxazole, hydroxy, —NHCO-substituted amino or —$SO_2Me$;

$R^3$ is hydroxy;

$R^4$ and $R^5$ are methyl;

$R^6$ is cyano, —$NO_2$, —$CF_3$, halo, alkyl, tetrazol or —$S(O)_2NR^{10}R^{11}$;

$R^7$ is hydrogen;

or $R^{10}$ and $R^7$ taken together with the atoms to which they are attached form an unsubstituted 5- to 7-membered ring or a 5- to 7-membered ring substituted with aryl.

* * * * *

UNITED STATES PATENT AND TRADEMARK OFFICE
CERTIFICATE OF CORRECTION

PATENT NO.    : 5,629,429
DATED         : May 13, 1997
INVENTOR(S)   : David R. Kronenthal et al It is certified that error appears in the above-identified patent and that said Letters Patent is hereby corrected as shown below:

In Claim 2, please correct line 59 to read as follows:
-- Y is a single bond, $-CH_2-$, $-C(O)-$, $-O-$, $-S-$ --

Signed and Sealed this

Seventeenth Day of February, 1998

Attest:

BRUCE LEHMAN

*Attesting Officer*          *Commissioner of Patents and Trademarks*